US00PP36954P2

(12) United States Plant Patent
Bedard

(10) Patent No.: US PP36,954 P2
(45) Date of Patent: Sep. 16, 2025

(54) CLIMBING ROSE PLANT NAMED 'WEKpuscalrako'

(50) Latin Name: *Rosa hybrida*
Varietal Denomination: WEKpuscalrako

(71) Applicant: Early Morning LLC, Lawrenceburg, IN (US)

(72) Inventor: Christian Bedard, Rancho Cucamonga, CA (US)

(73) Assignee: Early Morning LLC, Lawrenceburg, IN (US)

( * ) Notice: Subject to any disclaimer, the term of this patent is extended or adjusted under 35 U.S.C. 154(b) by 0 days.

(21) Appl. No.: 18/976,705

(22) Filed: Dec. 11, 2024

(51) Int. Cl.
*A01H 5/02* (2018.01)
*A01H 6/74* (2018.01)

(52) U.S. Cl.
USPC ..... Plt./109
CPC ..... *A01H 6/749* (2018.05)

(58) Field of Classification Search
USPC ..... Plt./109
CPC ..... A01H 5/0222
See application file for complete search history.

(56) References Cited

U.S. PATENT DOCUMENTS

| | | | |
|---|---|---|---|
| PP6,262 | P | 8/1988 | Stephens et al. |
| PP8,494 | P | 12/1993 | Tracy |
| PP9,389 | P | 12/1995 | Winchel |
| PP10,072 | P | 10/1997 | Carruth |
| PP17,346 | P2 | 1/2007 | Radler |
| PP19,776 | P2 | 2/2009 | Carruth |
| PP22,469 | P2 | 1/2012 | Carruth |
| PP22,571 | P2 | 3/2012 | Carruth |
| PP23,324 | P2 | 1/2013 | Bedard |
| PP23,692 | P3 | 7/2013 | Bedard |
| PP29,273 | P2 | 5/2018 | Fryer |

OTHER PUBLICATIONS

Weeks Roses: In Love Again, Wholesale Rose Catalog, Weeks Roses, 2025. Retrieved from the Internet: <URL:http://www.weeksroses.com/downloads/Catalogs_Digital/_WR25_Catalog_Digital.pdf>, 76 pages.

*Primary Examiner* — Kent L Bell
(74) *Attorney, Agent, or Firm* — McKee, Voorhees & Sease, PLC

(57) ABSTRACT

A new variety of Climbing rose suitable for garden decoration. having flowers of magenta. pink & white striped coloration.

1 Drawing Sheet

Classification: The present disclosure relates to a new *Rosa hybrida* plant.

Variety denomination: The new plant has the varietal denomination 'WEKpuscalrako'.

BACKGROUND OF THE INVENTION

This invention relates to a new and distinct variety of Climbing Rose. It has an unnamed non-disseminated seedling of my creation as its seed parent with the following genetic origin {seedling (not patented) x ('Blueberry Hill' (U.S. Plant Pat. No. 10,072) x 'Stephen's Big Purple' (U.S. Plant Pat. No. 6,262))} and an unnamed non-disseminated seedling of my creation as its pollen parent with the following genetic origin ('Candy Land' (U.S. Plant Pat. No. 19,776) x 'Rainbow Knock Out' (U.S. Plant Pat. No. 17,346)).

SUMMARY OF THE INVENTION

Among the features which distinguish the new variety from other presently available and commercial rose cultivars known to the applicant are the following combinations of characteristics: its unusual magenta, pink & white striped flower coloration, its large cluster composed of many flowers, its hairs on the receptacle of the flower, its variable sepal count and its vigorous growth. The plant has a spreading climbing growing habit, suitable for outdoor garden decoration.

Asexual reproduction of the new variety by budding as performed in Kern County, California, shows that the foregoing and other distinguishing characteristics come true to form and are established and transmitted through succeeding asexual propagations. 'WEKpuscalrako' may be asexually propagated by cuttings, budding and grafting. The budding and grafting successfully occurred on the plant/rootstock *Rosa hybrida* cv. 'Dr. Huey' (not patented).

COMPARISON WITH PARENTS

The new rose may be distinguished from its seed parent, an unnamed non-disseminated seedling of my creation by the following combination of characteristics: whereas 'WEKpuscalrako' bears double flowers (about 19 to 38 petals) of magenta, pink & white striped coloration, the unnamed non-disseminated seedling bears flowers of red-purple with a lavender eye coloration with significantly heavier petalage (about 40 to 45 petals). The new variety is classified as a Climbing rose with a spreading climbing growing habit with canes about 250 cm. to about 300 cm. in length, whereas the seed parent is a Floribunda rose with an upright somewhat spreading significantly shorter and narrower (about 110 to about 130 cm. in height and about 56 to about 75 cm. spread at the widest point), growing habit.

The new variety may be distinguished from its pollen parent, an unnamed non-disseminated seedling of my creation by the following combination of characteristics: whereas 'WEKpuscalrako' bears double flowers (about 19 to 38 petals) of magenta, pink & white striped coloration, the unnamed non-disseminated seedling bears flowers of fuchsia, purple and cream coloration with significantly lesser petalage (about 12 to 18 petals). The new variety is classified as a Climbing rose with a spreading climbing growing habit with canes about 250 cm. to about 300 cm. in length, whereas the pollen parent is a Shrub rose with a bushy upright moderately spreading significantly shorter and narrower (about 120 to about 140 cm. in height and about 100 to about 120 cm. spread at the widest point), growing habit.

COMPARISON WITH THE CLOSEST COMMERCIALLY AVAILABLE CULTIVAR

The new variety may be distinguished from its closest commercially available cultivar, 'WEKspitrib' (U.S. Plant Pat. No. 22,469) by the following combination of characteristics: whereas 'WEKpuscalrako' bears double flowers (about 19 to 38 petals) of magenta, pink & white striped coloration, 'WEKspitrib' bears flowers of wine purple striped with bright white coloration with significantly lesser petalage (about 8 to 12 petals). The new variety has a spreading climbing growing habit with canes about 250 cm. to about 300 cm. in length, whereas the closest commercially available cultivar has a spreading climbing significantly taller and wider growing habit with canes about 300 cm. to about 350 cm. in length.

BRIEF DESCRIPTION OF ILLUSTRATION

The accompanying photograph illustrates the new variety and shows the flowering thereof from bud to full bloom depicted in color as nearly correct as it is possible to make in a color illustration of the character. The branches used for the photograph came from 3 to 4 year-old rose plants of the new variety grown outdoors in Wasco, California in the month of November. Throughout this specification, color references and/or values are based upon The Colour Chart of The Royal Horticultural Society (1966) except where common terms of color definition are employed.

DESCRIPTION OF THE NEW VARIETY

The following description is of 3 to 4 year-old rose plants of the new variety grown outdoors in Wasco, California in the month of November. Phenotypic expression may vary with environmental, cultural and climatic conditions, as well as differences in conditions of light and soil.

FLOWER

The new variety usually bears its flowers in clusters of two to thirteen or more per stem. Flowers are borne in regular rounded clusters on strong short to long stems (about 18 to about 182 cm.). The cluster ranges from about 9.0 to about 21.0 cm. in diameter. Outdoors, the plant blooms abundantly and nearly continuously during the growing season. The flowers have a moderate fruity fragrance.

BUD

The peduncle is about 1.4 to about 7.4 cm. in length, of somewhat slender to average caliper (about 0.2 to about 0.4 cm. in diameter), and usually erect to sometimes moderately bending. It is moderately rough, with some stipitate glands, and few hairs. Peduncle color is between 146D and 146C often heavily suffused, especially on the side exposed to the sun, with between 187B and 187A.

Before the calyx breaks, the bud is about 0.8 to about 1.9 cm. in diameter at the widest point, about 0.9 to about 2.1 cm. in length, and pointed in shape. The surface of the bud bears between 14 to 24 foliaceous appendages with few stipitate glands, usually with slender entire foliaceous parts extending beyond the tip of the bud about ¼ or more of its length. Bud color is between 137B and 137A sometimes lightly suffused, especially on the side exposed to the sun, with between 187B and 187A.

The sepals are 5 to often between 6 to 8 per flower, about 1.7 to about 3.5 cm. in length and about 0.4 to about 1.0 cm. in width at the widest point. The outer surface color of the sepal is between 137B and 137A sometimes lightly suffused, especially on the side exposed to the sun, with between 187B and 187A. The outer surface of the sepal is somewhat rough and bears between 0 to 6 foliaceous appendages with few stipitate glands, and some hairs. The inner surface color of the sepal is near 146C broadly bordered by near 137A. After the sepals open, the inner surface color is often heavily suffused, especially on the area exposed to the sun, with between 187B and 187C. The inner surface of the sepal is covered with fine wooly tomentum: sepal margins are entire and lined with few stipitate glands and some hairs. The sepals are moderately permanent, and usually spear-shaped in shape with acute apices.

The receptacle of the flower is of short to somewhat long length (about 0.2 to about 0.8 cm.) and somewhat thin to average in caliper (about 0.4 to about 1.0 cm. in diameter). The receptacle is urn-shaped in form. Its surface is smooth with some hairs and few stipitate glands and with moderately thick fleshy walls. The receptacle color is between 144A and 146B often heavily suffused, especially on the side exposed to the sun, with between 187B and 187A.

As the petals open (after the calyx breaks), the bud is about 1.4 to about 2.4 cm. in diameter at the widest point, about 2.1 to about 3.0 cm. in length, and pointed to somewhat ovoid in form. The color of the under surfaces of the newly opened petals is irregularly striped and flecked with as dark as between 79A and 59A to as light as between 1C and 154D often lightly suffused with between 71B and 67A. At the point where the petal attaches, there is a moderately large zone of between 150C and 145C. The color of the upper surfaces of the newly opened petals is irregularly striped and flecked with as dark as between 71A and 59A to as light as between 1C and 154D often lightly suffused with between 71B and 67A. At the point where the petal attaches, there is a somewhat large zone of near 150C.

BLOOM

When fully open, the bloom ranges from about 6.7 to about 10.6 cm. in diameter. Petalage is double with about 19 to 38 petals and about 0 to 7 petaloids irregularly arranged. When partially open, the bloom form is cupped, and the petals are loosely spiraled to cupped with petal edges somewhat reflexed inward to straight. When fully open, the bloom form is more cupped, and the petals are loosely cupped to somewhat undulated with petal edges somewhat reflexed outward.

PETALS

The substance of the petals is moderately heavy and of medium to somewhat thick thickness, with upper surfaces moderately satiny to slightly shiny and under surfaces moderately shiny. The petals are about 3.6 to about 5.5 cm. in length and about 3.3 to about 5.8 cm. in width at the widest point. Petal margins are entire.

The outer petals are broadly rounded to somewhat obovate in shape with rounded apices.

The inner petals are moderately obovate in shape with rounded apices.

Petaloids are about 1.4 to about 4.8 cm. in length and about 0.5 to about 4.2 cm. in width at the widest point. Petaloids are irregularly shaped sometimes broadly rounded to sometimes moderately obovate to somewhat oblanceolate to subulate with rounded to sometimes lacerated apices.

NEWLY OPENED FLOWER

The under-surface color of the outer, intermediate and inner petals is irregularly striped and flecked with as dark as between 60B and 60A to as light as between 9D and 155C often lightly suffused with between 71B and 67A. At the point where the petal attaches, there is a somewhat large zone of between 154D and 1D. The upper surface color of the outer, intermediate and inner petals is irregularly striped and flecked with as dark as between darker than 71A and 60A to as light as between 9D and 155C often lightly suffused with between 71B and 67A. At the point where the petal attaches, there is a somewhat large zone of near 2B.

The under and upper surface colors of the petaloids are similar in coloration to the upper and under surfaces of the intermediate and inner petals.

The general tonality of the newly opened flower is irregularly striped and flecked with as dark as between darker than 71A and 60A to as light as between 9D and 155C often lightly suffused with between 71B and 67A.

THREE-DAY-OLD FLOWER

The under-surface color of the outer, intermediate and inner petals is irregularly striped and flecked with as dark as between 70A and 60A to as light as between 158C and 155C often lightly suffused with between 71B and 67A. At the point where the petal attaches, there is a moderately large zone of between 155A and 155C. The upper surface color of the outer, intermediate and inner petals is irregularly striped and flecked with as dark as between darker than 71A and 60A to as light as between 158C and 155C often lightly suffused with between 71B and 67A. At the point where the petal attaches, there is a moderately large zone of between lighter than 2D and 155A.

The under and upper surface colors of the petaloids are similar in coloration to the upper and under surfaces of the intermediate and inner petals.

The general tonality of the three-day-old flower is irregularly striped and flecked with as dark as between darker than 71A and 60A to as light as between 158C and 155C often lightly suffused with between 71B and 67A.

On the spent bloom, the petals usually drop off cleanly.

In November in Wasco, California, blooms on the bush growing outdoors generally last about four to five days. Cut roses from plants grown outdoors and kept at normal indoor living temperatures generally last about four to five days.

MALE REPRODUCTIVE ORGANS

Stamens are many in number (average about 105) and are arranged regularly about the pistils: a few are mixed with petaloids. The filaments are of short to long length (about 0.3 to about 1.5 cm.) most with anthers. Filaments are between 4B and 5C in color sometimes lightly suffused with near 60B. The anthers are of medium to somewhat large size for the class and all open approximately at the same time. Anther color when immature is near 21B on the external part and near 12D on the internal part. Anther color at maturity is near 164C on the external part and near 200A on the internal part. Pollen is moderately abundant and between 18C and 19C in color.

FEMALE REPRODUCTIVE ORGANS

Pistils vary in number (average about 52). The styles are moderately even, somewhat short to average in length (about 0.5 to about 0.9 cm.), average to somewhat heavy in caliper, and loosely bunched. Stigma color is between 17D and 16C. Style color is between 1D and 154D often heavily suffused with between 60A and 60B. Ovaries are usually all enclosed in the calyx. The ovaries are of medium to somewhat large size and between 158A and 158B in color.

Hips have not been observed on this variety when grown in Wasco, California.

FOLIAGE

The compound leaves are usually comprised of three to seven leaflets and are borne abundantly. The seven-leaflet leaves are about 9.0 to about 17.5 cm. in length and about 6.3 to about 13.2 cm. in width at the widest point, moderately leathery to somewhat crisp in texture on both sides, and glossy in finish on the upper side and somewhat semi-glossy to matte in finish on the underside. The leaves have a pinnate venation pattern. The terminal leaflets are about 3.6 to about 7.7 cm. in length and about 2.0 to about 5.1 cm. in width at the widest point, shaped ovate to somewhat oval with acute apices and rounded to somewhat acute bases. Their margins are usually simply serrate.

The upper surface color of the mature leaf is between 137A and 146A. The under-surface color of the mature leaf is between 146C and 138B. The under and upper colors of the leaf veins on the mature leaf are similar in coloration to the upper and under surfaces colors of the mature leaf. The upper surface color of the young leaf is between 138A and 146C, often lightly suffused with between 187A and 187B. The under-surface color of the young leaf is between 146B and 146C, often lightly suffused with between 187B and 187A. The under and upper colors of the leaf veins on the young leaf are similar in coloration to the upper and under surfaces colors of the young leaf.

The rachis is about 3.5 to about 7.1 cm. in length, about 0.1 to about 0.2 cm in width at the widest point, and rough. The upper side is shallowly grooved with few hairs and few stipitate glands on the edges of the grooves. The under side of the rachis is rough with few stipitate glands and few small prickles. The rachis color is near 145C on the under side and near 146C on the upper side, often heavily suffused on the young leaves with between 187B and 187C.

The stipules are about 1.0 to about 2.4 cm. in length and of medium to wide width (about 0.5 to about 1.2 cm.) with medium to moderately long straight points that usually turn out at an angle of more than 45 degrees and sometimes recurve toward the stem. The under and upper surface color of the stipule is between 137B and 137C sometimes lightly suffused with between 187B and 187C. The upper and under surfaces of the stipules are smooth in texture.

The petiole is moderately light to average in caliper and rough. The upper side is shallowly grooved with few hairs and few stipitate glands on the edges of the grooves. The under side of the petiole is rough with few stipitate glands and few small prickles. The petiole is about 0.2 to about 1.5 cm. in length and about 0.1 to about 0.2 cm in width at the widest point. The petiole color is near 145C on the underside and near 146C on the upper side, often heavily suffused on the young leaves with between 187B and 187C.

The plant displays an above average degree of resistance to powdery mildew (*Sphaerotheca pannosa*), downy mildew (*Peronospora sparsa*), and rust (*Phragmidium* sp.) as compared to other commercial varieties grown under comparable conditions in Wasco, California. The plant's winter hardiness and drought/heat tolerance are yet to be determined.

GROWTH

The plant has a spreading climbing tall growing habit with canes about 250 cm. to about 300 cm. in length with full branching. It displays vigorous growth and the canes are of somewhat light to medium caliper for the class (about 1.1 to about 1.7 cm. in diameter at the widest point).

The color of the major stems is between 146B and 152B. The major stems are rough in texture and they bear some large prickles that are about 0.4 to about 0.9 cm. in length. The large prickles are angled slightly downward with a moderately long narrow oval base: prickle color is between 165C and 164B sometimes lightly suffused with near 201D. The major stem bears few small prickles of similar shape and coloration.

The color of the branches is between 146C and 146A often moderately suffused with between 187B and 187C. The branches are rough in texture and they bear some large prickles which are of similar size and shape to the large prickles on the major stems; prickle color is between 164C and 163C often heavily suffused with between 187B and 187C. The branches bear few small prickles of similar shape and coloration.

The color of the new shoots is between 146C and 137C often moderately suffused with between 187B and 187C. The new shoots are rough in texture and they bear some large prickles which are of similar size and shape to the large prickles on the major stems; prickle color is near 162A often heavily suffused with between 187B and 187C. The shoots bear few small prickles of similar shape and coloration.

I claim:

1. A new and distinct Climbing rose plant of the variety designated 'WEKpuscalrako' substantially as described and illustrated herein.

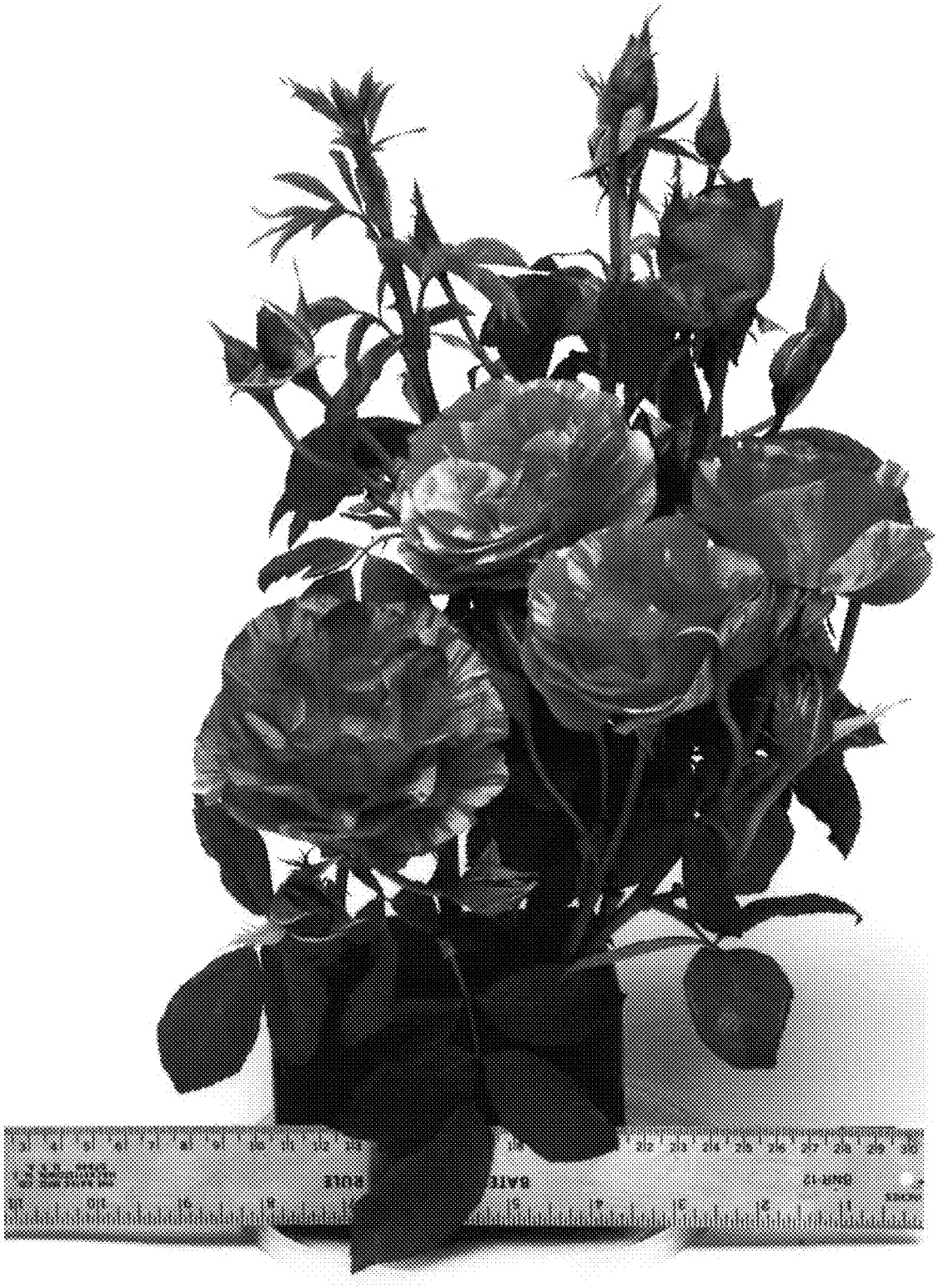

* * * * *